US00PP19621P2

(12) United States Plant Patent
Watanabe

(10) Patent No.: US PP19,621 P2
(45) Date of Patent: Jan. 6, 2009

(54) ***PACHYSANDRA* PLANT NAMED 'HAKUREI'**

(50) Latin Name: *Pachysandra terminalis*
Varietal Denomination: Hakurei

(76) Inventor: Kenji Watanabe, 1602-2 Takaraghonmachi, Utsunomiya city, Tochigi prefecture, 3200075 (JP)

( * ) Notice: Subject to any disclaimer, the term of this patent is extended or adjusted under 35 U.S.C. 154(b) by 35 days.

(21) Appl. No.: 11/823,581

(22) Filed: Jun. 28, 2007

(51) Int. Cl.
*A01H 5/00* (2006.01)

(52) U.S. Cl. ..... Plt./226

(58) Field of Classification Search ..... None
See application file for complete search history.

*Primary Examiner*—Wendy C. Haas
(74) *Attorney, Agent, or Firm*—Audrey Charles

(57) ABSTRACT

A new and distinct cultivar of *Pachysandra* plant named 'Hakurei', characterized by its new foliage growth of creamy white with grayed-green venation maturing over time to yellowish green.

1 Drawing Sheet

Figure 1:
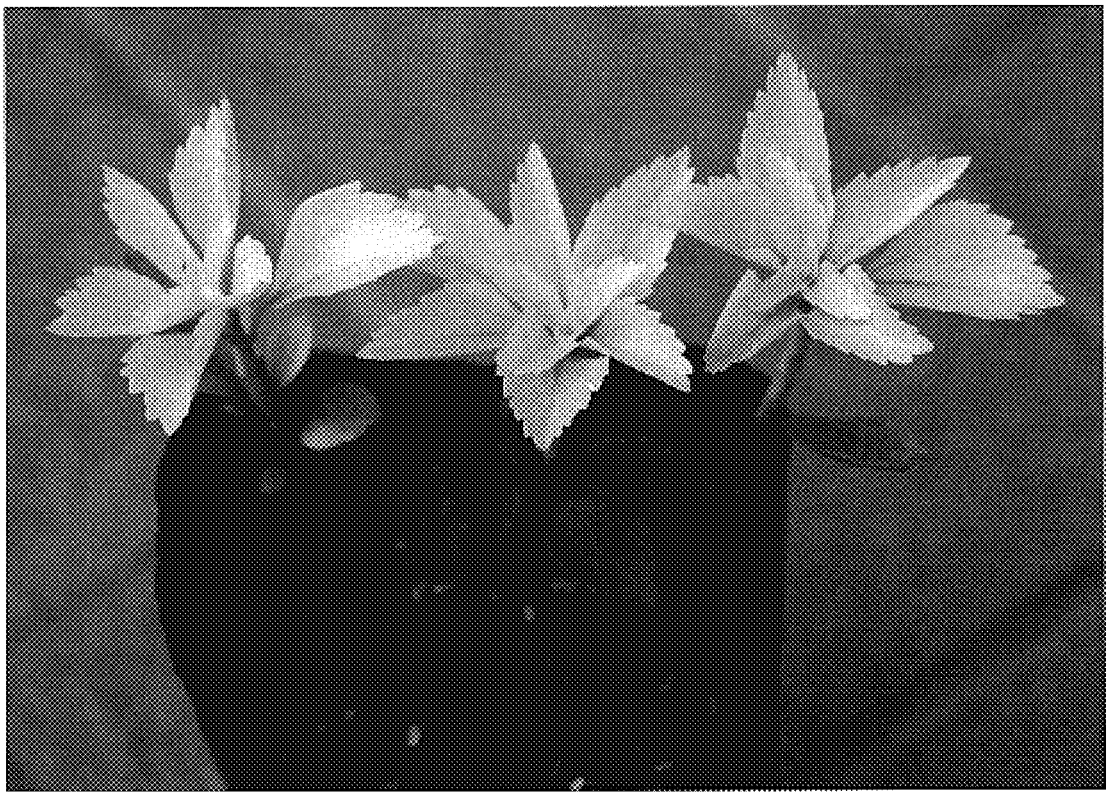

Latin name of genus and species of plant claimed: *Pachysandra terminalis.*
Variety denomination: 'Hakurei'.

BACKGROUND OF THE INVENTION

The present invention relates to a new and distinct cultivar of *Pachysandra* plant botanically known as *Pachysandra terminalis* Michx. and hereinafter referred to by the cultivar name 'Hakurei'.

The new cultivar originated in a controlled selection program in Utsunomiya, Japan during 2005. 'Hakurei' is a branch sport of *Pachysandra terminalis.* The object of the program was the development of *Pachysandra* cultivars with unique foliage color.

The new *Pachysandra* cultivar is a naturally occurring sport of *Pachysandra terminalis,* not patented, characterized by its dark green-colored foliage. The new cultivar was discovered as a branch sport and selected in January 2005 in a controlled environment at Utsunomiya, Japan.

Asexual reproduction of the new cultivar by terminal stem cuttings since July 2005 at Utsunomiya, Japan has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Hakurei' as a new and distinct cultivar of *Pachysandra* plant:

1. New growth is a creamy white with grayed-green venation, and
2. Mature foliage is yellowish green.

Plants of the new cultivar differ from plants of the parent primarily in foliage coloration.

Of the few commercially available *Pachysandra* cultivars known to the inventor, the most similar in comparison to the new cultivar is the parent *Pachysandra terminalis* 'Variegata', an unpatented cultivar. However, in side by side comparisons, plants of the new cultivar differ from plants of 'Variegata' in the following characteristics:

1. Plants of the new cultivar have immature foliage of creamy white with greyed-green venation while the plants of 'Variegata' have immature foliage of mottled variegation; and
2. Plants of the new cultivar have foliage that matures to a yellowish green, while plants of 'Variegata' have mature foliage of mottled variegation.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Hakurei'. The plants were grown for 8 months in a 9 cm wide and 12 cm deep pot outdoors in Utsunomiya, Japan.

FIG. 1 illustrates the overall growth and habit of 'Hakurei'.

DETAILED BOTANICAL DESCRIPTION

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Apr. 10, 2007 under natural light conditions in West Chicago, Ill. and confirmed on May 17, 2007 under natural light conditions in Takarazuka, Japan.

The following descriptions and measurements describe the plants produced from cuttings taken from stock plants and grown outdoors in Utsunomiya, Japan with day temperatures ranging from 23° C. to 30° C. (75° F. to 87° F.) and night temperatures ranging from 1° C. to 8° C. (34° F. to 47° F.). The plants were grown in a 9 cm wide and 12 cm deep pot for 8 months.

Botanical classification: *Pachysandra terminalis* cultivar 'Hakurei'.

Parentage:

*Parent.*—*Pachysandra terminalis* Michx.

*Family.*—Buxaceae.

Propagation:

*Type cutting.*—Softwood.

*Time to initiate roots.*—Approximately 15 to 30 days.

*Time to produce a rooted cutting.*—Approximately 30 to 45 days.

*Root description.*—Hairy, rhizome.

Plant Description:

*Commercial crop time.*—Approximately 4 to 8 weeks from a rooted cutting to finish in a 5 cm pot.

*Growth habit and general appearance.*—Low growing ground cover. Evergreen, procumbent subshrub with fleshy often rhizome-like shoots and short, erect branches with leaves clustered at the apex.

*Size.*—Height from soil level to top of plant plane: Approximately 7 cm. Width: Approximately 13 cm.

*Branching habit.*—Branches arise from rhizome. Quantity of main branches per plant: Approximately 3 per 9 cm wide and 12 cm deep pot.

*Branch.*—Strength: Stems somewhat fleshy, flexible. Length: Approximately 4.7 cm. Diameter: Approximately 4.8 mm. Length of central internode: Approximately 4.0 mm. Texture: Glabrous. Color of young stem: 155A. Color of mature stem: 143C.

Foliage description:

*General description.*—Quantity of leaves per main branch: Approximately 10. Fragrance: None noted. Form: Simple. Arrangement: Whorled, clustered at apex.

*Leaves.*—Aspect: Obtuse angle to stem. Shape: Oblong rhombic to oblong obovate. Margin: Entire. Apex: Coarsely dentate. Base: Cuneate. Venation pattern: Pinnate. Length of mature leaf: Approximately 2.9 cm not including the petiole. Width of mature leaf: Approximately 2.2 cm. Texture of upper and lower surfaces: Glabrous. Color of upper surface of young foliage: 155C with venation 191B. Color of lower surface of young foliage: 155A with venation 139B. Color of upper surface of mature foliage: 146A with indistinguishable venation. Color of lower surface of mature foliage: 143C with indistinguishable venation.

*Petiole.*—Length: Approximately 1.4 cm. Diameter: Approximately 2.0 mm. Texture: Glabrous. Color of young petiole: 139D. Color of mature petiole: 139C.

Flowering description: Flowers not observed.

Seed and fruit production: Neither seed nor fruit production has been observed.

Disease and pest resistance: Resistance to pathogens and pests common to *Pachysandra* has not been observed.

What is claimed is:

1. A new and distinct cultivar of *Pachysandra* plant named 'Hakurei', substantially as herein shown and described.

* * * * *